United States Patent

Chee et al.

[11] Patent Number: 6,093,843
[45] Date of Patent: Jul. 25, 2000

[54] 4-HYDROXYBIPHENYL HYDRAZIDE DERIVATIVES

[75] Inventors: Gaik-Lean Chee, Guelph; Sheldon Bernard Park; Mark Archiel Dekeyser, both of Waterloo, all of Canada

[73] Assignees: Uniroyal Chemical Company, Inc., Middlebury, Conn.; Uniroyal Chemical Co./CIE., Elmira, Canada

[21] Appl. No.: 09/413,072

[22] Filed: Oct. 6, 1999

[51] Int. Cl.$^7$ .................................................. C07C 271/20
[52] U.S. Cl. ................................................ 560/27; 560/24
[58] Field of Search .......................... 560/25, 27

[56] References Cited

U.S. PATENT DOCUMENTS 5,367,093  11/1994  Dekeyser et al. .

*Primary Examiner*—Gary Geist
*Assistant Examiner*—Leigh C. Maier
*Attorney, Agent, or Firm*—Daniel Reitenbach

[57] ABSTRACT

Compounds having the formula:

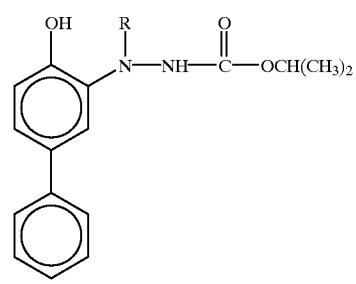

(I)

wherein R is hydrogen or $CO_2CH(CH_3)_2$, useful as intermediates in the preparation of the miticide bifenazate, methods for their preparation, and methods for the preparation of bifenazate.

24 Claims, No Drawings

4-HYDROXYBIPHENYL HYDRAZIDE DERIVATIVES

FIELD OF THE INVENTION

This invention relates to certain 4-hydroxybiphenyl hydrazide derivatives useful as intermediates in the preparation of isopropyl-2-(4-methoxy-[1,1'-biphenyl]-3-yl) hydrazine carboxylate (bifenazate).

BACKGROUND OF THE INVENTION

U.S. Pat. No. 5,367,093 describes a method for the preparation of the miticidal phenylhydrazine derivative, isopropyl-2-(4-methoxy-[1,1'-biphenyl]-3-yl)hydrazine carboxylate (bifenazate), using a six-step procedure which comprises the undesirable steps of preparation and reduction of a diazonium salt.

Certain phenylhydrazine derivatives can be prepared using the methods described in U.S. Pat. No. 4,864,032 (amination of Grignard); in Mitchell, J. Org. Chem. 59: 682 (1994) (amination of electron-rich arenes); and in Lenarsic, J. Org. Chem. 64: 2558 (1999) (by electrophilic azodicarboxylates).

It is the purpose of this invention to provide new intermediates useful in the preparation of bifenazate. It is also a purpose of this invention to provide a new method for the preparation of bifenazate.

SUMMARY OF THE INVENTION

The present invention relates to compounds of the formula:

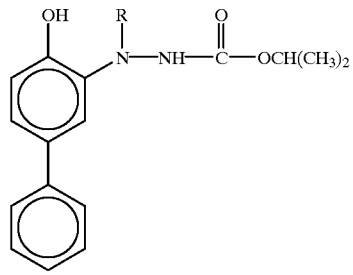

(I)

wherein R is hydrogen (IA) or isopropyl ester ($CO_2CH(CH_3)_2$) (IB).

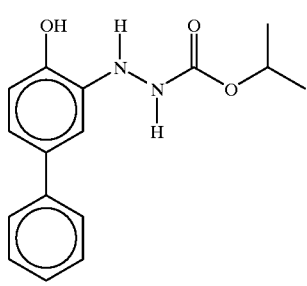

(IA)

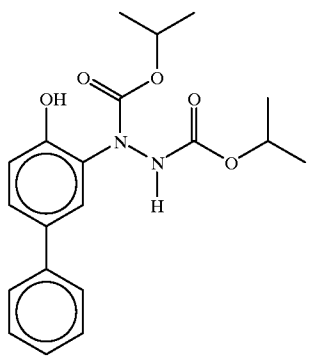

(IB)

The compounds of formulas IA and IB are useful as intermediates in the preparation of bifenazate.

The present invention also relates to a method for preparing the compound of IA which comprises hydrolyzing the compound of IB in the presence of an effective amount of a base in a suitable organic solvent.

The present invention further relates to a method for preparing bifenazate comprising methylating Compound IA in the presence of an effective amount of a methylating agent and a base, in a suitable solvent.

DETAILED DESCRIPTION OF THE INVENTION

The compounds of this invention can be prepared as described below in SCHEME 1.

1. Amination

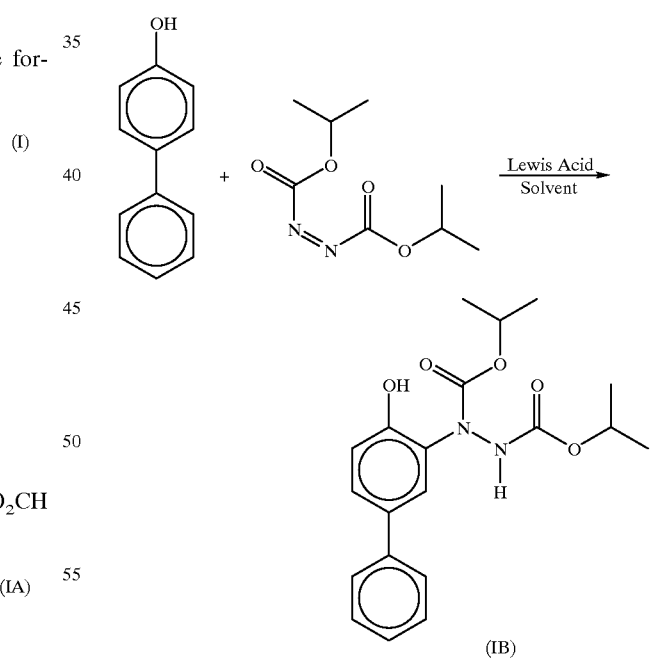

4-Hydroxybiphenyl is reacted with di-isopropyl azodicarboxylate in the presence of an effective amount of Lewis acid in a suitable solvent, to produce Compound IB. Useful Lewis acids include, e.g., boron. trifluoride etherate and aluminum chloride. The concentration of the Lewis acid to the 4-hydroxybiphenyl in the reaction mixture can be between about 1:0.2 to about 1:1.1 (mol/mol), preferably about 1:1.1 (mol/mol). Suitable organic solvents are those organic solvents which are not deleterious to the amination reaction and include, e.g., ethyl acetate, dichloromethane, toluene, and glyme. The temperature of the reaction mixture should be from about 0° C. to about 60° C., preferably at room temperature.

2. Selective Hydrolysis

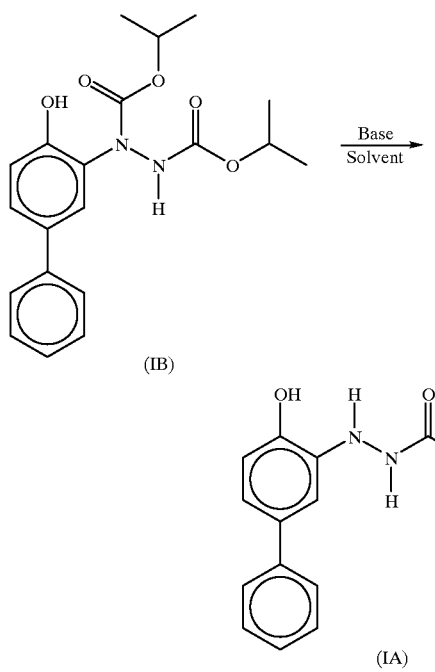

(IB)

(IA)

Compound IB is treated with an effective amount of a base in a suitable organic solvent to produce Compound IA. Useful base compounds are those base compounds which can hydrolyze the ester functionality and include, e.g., sodium hydroxide and potassium hydroxide. The concentration of the base to Compound IB can be between about 7:1 to about 10:1 (mol/mol), preferably about 9:1 (mol/mol). Suitable organic solvents are those organic solvents which are not deleterious to the hydrolysis reaction and include, e.g, toluene, dimethyl sulfoxide, and glyme. Preferably, the temperature of the organic solvent should be above room temperature and below 110° C.

Compound IA is then methylated in the presence of an effective amount of a methylating agent and a base, in a suitable organic solvent. For the purpose of this invention, a "methylating agent" is any compound which is capable of substituting a methyl group for the hydrogen atom in the 4-hydroxy group in Compound IA. Useful methylating agents include, e.g., dimethylsulfate and methyl iodide. The concentration of methylating agent to Compound IA can be between about 1:1 to about 1:1.2 (mol/mol), preferably about 1:1 (mol/mol). Useful base compounds are those base compounds which can depronate phenols and include, e.g., sodium carbonate and potassium carbonate. The concentration of base to Compound IA can be between about 1:1 to about 3:1 (mol/mol), preferably about 2:1 (mol/mol). Suitable organic solvents are those organic solvents which are not deleterious to the methylation reaction and include, e.g., toluene and acetone. The methylation reaction can be conducted at about room temperature. The methylation process is exemplified below in Scheme 2.

SCHEME 2

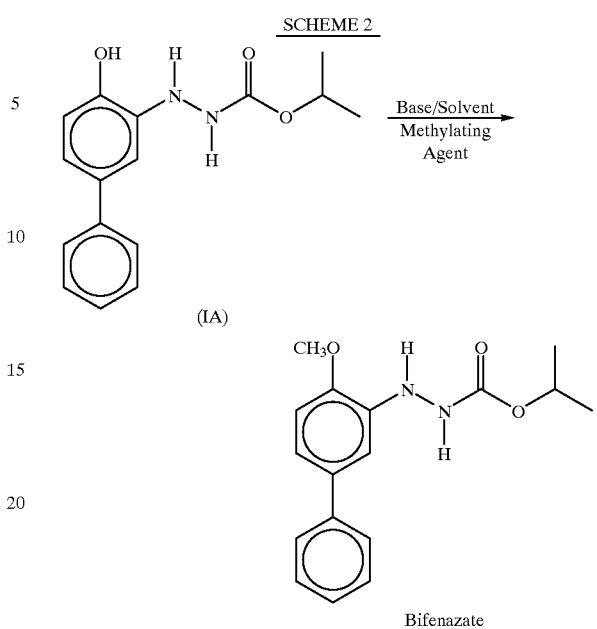

(IA)

Bifenazate

The following examples are provided to illustrate the present invention.

EXAMPLE 1

Preparation of 1,2-Hydrazinedicarboxylic acid, 1-(4-hydroxy-[1,1'-biphenyl]-3-yl)-, bis(1-methylLethyl) ester (Compound IB)

To a solution of 4-hydroxybiphenyl (5.50 g) in ethyl acetate (60 mL) at room temperature was added boron trifluoride etherate (4.1 mL). The resultant mixture was cooled to −5° C., added dropwise di-isopropyl azodicarboxylate (6.3 mL), and stirred at that temperature for 30 min. and then stirred at room temperature for two hours. The mixture was then quenched with water (100 mL) and extracted with ethyl acetate (50 mL). The organic phase was separated, dried over magnesium sulfate, and concentrated under vacuum to leave an oil which was chromatographed on silica gel using 20–30% ethyl acetate/hexane to produce Compound IB as beige-colored solid (10.65 g, 88% yield) . $^1$H-NMR (ppm, in CDCl$_3$): m(12)1.30; m(2)5.04; m(2)7.10; m(1)7.32; dd(2)7.43; m(3)7.51–7.55; br s(1)8.53.

EXAMPLE 2

Preparation of hydrazinecarboxylic acid, 2-(4-hydroxy-[1.1'-biphenyl]-3-yl)-, 1-methylethyl ester (Compound IA)

Potassium hydroxide (5.0 g) was added to a stirred suspension of Compound IB produced above in Example 1 (5.15 g) in toluene (50 mL). The resultant purple mixture was bubbled with nitrogen for 20 min., and then heated at 45° C. for 4 days. The mixture was then cooled to 0° C. and then 6M HCl was added to the mixture until the pH of the mixture was about 1. The mixture was then extracted with ethyl acetate. The organic phase was separated, washed with brine, dried over magnesium sulfate, and concentrated to a brown solid. Recrystallization from toluene produced Compound IA as beige-colored powder (3.35 g, 850 yield). $^1$H-NMR (ppm, in CDCl$_3$): d(6)1.81; septet(1)5.04; br d(1) 5.91; br s(1)6.61; d(1)6.74; dd(1)7.01; d(1)7.14; dd(1)7.32; dd(2:)7.42; dd(2)7.61.

EXAMPLE 3

Preparation of hydrazinecarboxylic acid, 2-(4-methoxy-[1,1'-biphenyl]-3-yl)-, 1-methylethyl ester (bifenazate)

A suspension of Compound IA prepared above in Example 2 (2.63 g) and potassium carbonate (2.50 g) in acetone (40 mL) was bubbled with nitrogen for 20 minutes. Dimethyl sulfate (0.96 mL) at room temperature was then added to the suspension. After 2 hours, the resultant reaction mixture was cooled in ice bath. 2M HCl was then cautiously added (ca. 30 mL) to the reaction mixture until the pH of the reaction mixture was about 1. The reaction mixture was then concentrated to remove most acetone. The solid formed from the concentrated reaction mixture was filtered, washed with water, hexane, and dried under air with suction to produce bifenazate (2.60 g). $^1$H-NMR spectral data is consistent with the $^1$H-NMR reported for bifenazate in U.S. Pat. No. 5,367,093.

What is claimed is:

1. A compound having the formula:

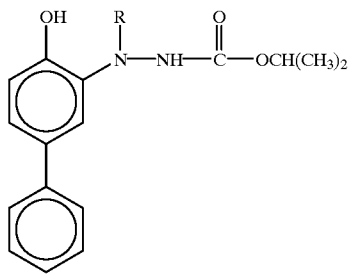

(I)

wherein R is hydrogen or $CO_2CH(CH_3)_2$.

2. A compound as recited in claim 1 having the formula:

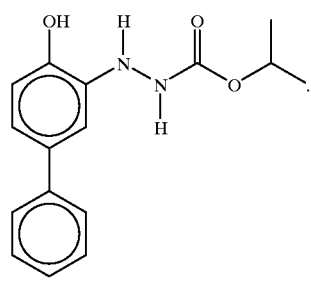

(IA)

3. A compound as recited in claim 1 having the formula:

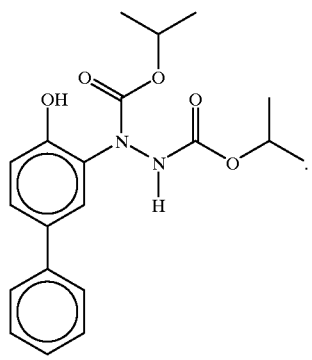

(IB)

4. A method for preparing a compound of the formula:

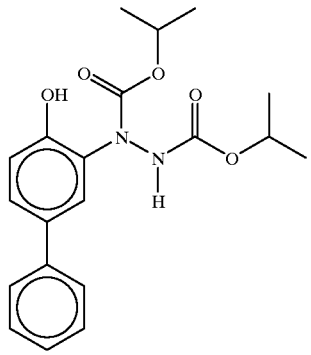

(IB)

which method comprises reacting 4-hydroxybiphenyl with di-isopropyl azodicarboxylate in the presence of an effective amount of a Lewis acid, in a suitable solvent.

5. A method as recited in claim 4 wherein the concentration of the Lewis acid to the 4-hydroxybiphenyl in the reaction mixture is between about 1:0.2 to about 1:1.1 (mol/mol).

6. A method as recited in claim 5 wherein the concentration of the Lewis acid to the 4-hydroxybiphenyl in the reaction mixture is about 1:1.1 (mol/mol).

7. A method as recited in claim 5 wherein the Lewis acid is selected from the group consisting of boron trifluoride etherate, and aluminum chloride.

8. A method as recited in claim 4 wherein the organic solvent is selected from the group consisting of ethyl acetate, dichloromethane, toluene, glyme, and diethyl ether.

9. A method for preparing a compound of the formula:

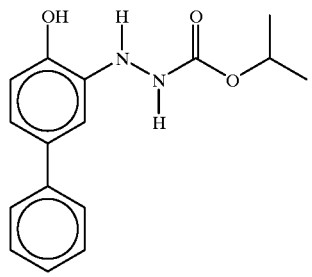

(IA)

which comprises hydrolyzing a compound of the formula:

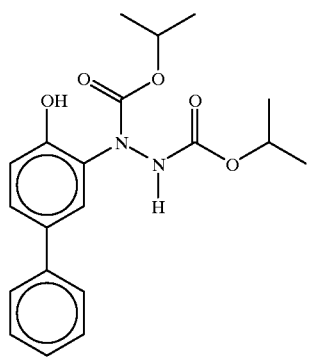

(IB)

in the presence of an effective amount of base and a suitable organic solvent.

10. A method as recited in claim 9 wherein the base is selected from the group consisting of sodium hydroxide and potassium hydroxide.

11. A method as recited in claim 9 wherein the organic solvent is selected from the group consisting of toluene, dimethyl sulfoxide, and glyme.

12. A method as recited in claim 9 conducted at a temperature between room temperature and 110° C.

13. A method as recited in claim 9 wherein the concentration of base to Compound IB is about 7:1 to about 10:1 (mol/mol).

14. A method as recited in claim 13 wherein the concentration of base to Compound IB is about 7:1 (mol/mol).

15. A process for the preparation of a compound of the formula:

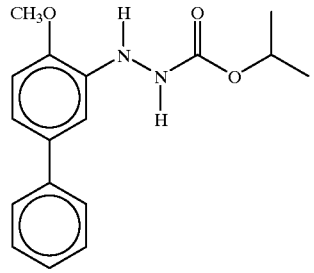

which process comprises methylating a compound of the formula:

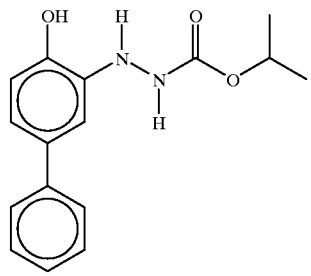

(IA)

in the presence of an effective amount of a methylating agent and a base, and a suitable organic solvent.

16. A method as recited in claim 15 wherein the methylating agent is selected from the group consisting of dimethylsulfate and methyl iodide.

17. A method as recited in claim 15 wherein the base is selected from the group consisting of sodium carbonate and potassium carbonate.

18. A method as recited in claim 15 wherein the organic solvent is selected from the group consisting of toluene and acetone.

19. A method as recited in claim 15 conducted at about room temperature.

20. A method as recited in claim 15 wherein the concentration of methylating agent to Compound IA is about 1:1 to about 1.2:1 (mol/mol).

21. A method as recited in claim 20 wherein the concentration of methylating agent to Compound IA is between about 1:1 (mol/mol).

22. A method as recited in claim 15 wherein the concentration of base to Compound IA is about 1:1 to about 3:1 (mol/mol).

23. A method as recited in claim 22 wherein the concentration of base to Compound IA is about 2:1 (w/w).

24. A process for the preparation of a compound of the formula:

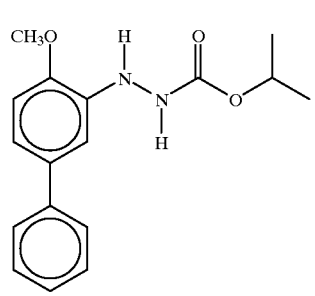

(I)

which process comprises:

(a) reacting 4-hydroxybiphenyl with di-isopropyl azodicarboxylate in the presence of an effective amount of Lewis acid, in a suitable solvent, to produce a compound of the formula:

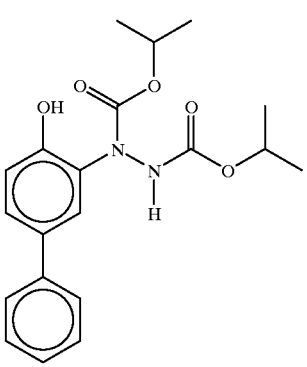

(IB)

(b) hydrolyzing the compound of the formula IB in the presence of an effective amount of base and a suitable organic solvent, to produce a compound of the formula:

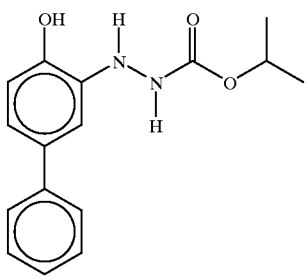
(IA)
and
(c) methylating the compound of formula IA in the presence of an effective amount of a methylating agent and a base, in a suitable organic solvent, to produce the compound of the formula:
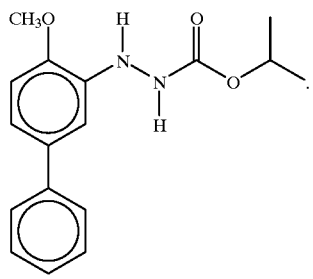
(I)
* * * * *